United States Patent [19]

Michaely

[11] Patent Number: 5,026,896

[45] Date of Patent: Jun. 25, 1991

[54] TRISUBSTITUTED BENZOIC ACID INTERMEDIATES

[75] Inventor: William J. Michaely, El Cerrito, Calif.

[73] Assignee: ICI Americas Inc., Wilmington, Del.

[21] Appl. No.: 520,345

[22] Filed: May 8, 1990

Related U.S. Application Data

[60] Continuation of Ser. No. 386,649, Jul. 31, 1989, abandoned, which is a division of Ser. No. 272,841, Nov. 18, 1988, abandoned.

[51] Int. Cl.$^5$ .................. C07C 205/06; C07C 321/28; C07C 255/50; C07C 63/10

[52] U.S. Cl. .................................... 560/23; 558/411; 558/412; 558/425; 560/9; 560/11; 560/16; 560/65; 562/429; 562/432; 562/438; 562/840; 562/868; 568/39; 568/41; 568/425

[58] Field of Search ...................... 558/441, 412, 425; 560/9, 11, 16, 23, 65; 562/429, 432, 438, 840, 868; 568/39, 41, 425

[56] References Cited

FOREIGN PATENT DOCUMENTS 0108526  5/1984  European Pat. Off. .

OTHER PUBLICATIONS

CA, 107(13):115304x, Sep. 1987.

*Primary Examiner*—Jose G. Dees
*Assistant Examiner*—Vera C. Clarke
*Attorney, Agent, or Firm*—Edwin H. Baker

[57] ABSTRACT

Novel trisubstituted benzoic acid intermediates which are useful in the preparation of certain herbicidal 2-(2,3,4-trisubstituted benzoyl)-1,3-cyclohexanediones are described.

18 Claims, No Drawings

TRISUBSTITUTED BENZOIC ACID INTERMEDIATES

This is a continuation of application Ser. No. 07/386,649 filed July 31, 1989, now abandoned, which is a divisional of application Ser. No. 07/272,841, filed Nov. 18, 1988, now abandoned.

BACKGROUND OF THE INVENTION

Certain 2-(2'3'4'tri-substituted benzoyl)-1,3-cyclohexanedione herbicides are described in U.S. Pat. No. 4,780,127, issued Oct. 25, 1988, U.S. application Ser. No. 129,026, filed Dec. 4, 1987; and a U.S. application entitled 2-(2',3',4'-trisubstituted benzoyl)-1,3-cyclohexanediones, with William J. Michaely, Inventor, filed herewith, and all incorporated herein by reference.

The above-described herbicidal compounds can have the following structural formula

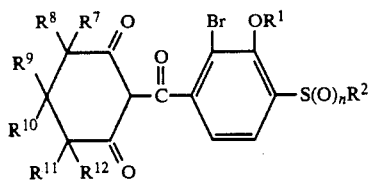

wherein $R^7$ through $R^{12}$ are hydrogen or $C_1$–$C_4$ alkyl; $R^1$ is $C_1$–$C_4$ alkyl, $C_1$–$C_4$ haloalkyl, $CH_2CH_2$—$OCH_3$, $CH_2CH_2OC_2H_5$, $CH_2CH_2SCH_3$, or $CH_2CH_2SC_2H_5$; $R^2$ is $C_1$–$C_4$ alkyl; and n is the integer 0 or 2.

These herbicides can be prepared by reacting a dione of the structural formula

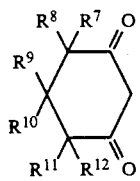

wherein $R^7$ through $R^{12}$ are as defined with a mole of trisubstituted benzoyl chloride of the structural formula

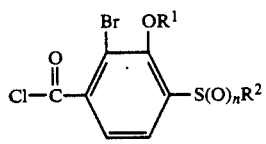

wherein n, $R^1$ and $R^2$ are as defined above.

DESCRIPTION OF THE INVENTION

This invention has several embodiments which are as follows:

Embodiment A relates to novel intermediate compounds having the structural formula

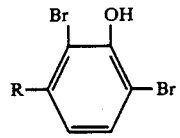

wherein R is $C_1$–$C_2$ alkyl, preferably methyl; formyl; cyano; carboxy; or —$CO_2R^a$ where $R^a$ is $C_1$–$C_4$ alkyl, preferably ethyl; most preferably R is —$CO_2C_2H_5$.

Embodiment B relates to novel intermediate compounds having the structural formula

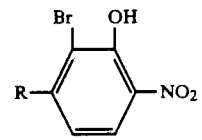

wherein R is $C_1$–$C_2$ alkyl, preferably methyl; formyl; cyano; carboxy or —$CO_2R^a$ wherein $R^a$ is $C_1$–$C_4$ alkyl, preferably ethyl; most preferably R is —$CO_2C_2H_5$.

Embodiment C relates to novel intermediate compounds having the structural formula

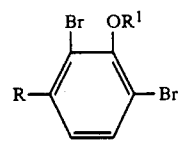

wherein R is $C_1$–$C_2$ alkyl, preferably methyl; formyl; cyano; carboxy or —$CO_2R^a$ wherein $R^a$ is $C_1$–$C_4$ alkyl, preferably ethyl, most preferably R is —$CO_2C_2H_5$ and $R^1$ is $C_1$–$C_4$ alkyl; preferably $C_1$–$C_2$ alkyl; $C_1$–$C_4$ haloalkyl; —$CH_2CH_2OCH_3$; —$CH_2CH_2OC_2H_5$; —$CH_2CH_2SCH_3$ or —$CH_2CH_2SC_2H_5$, with the proviso that when R is carboxy, then $R^1$ is —$CH_2CH_2OCH_3$; —$CH_2CH_2OC_2H_5$; —$CH_2CH_2SCH_3$ or —$CH_2CH_2SC_2H_5$.

Embodiment D relates to novel intermediate compounds having the structural formula

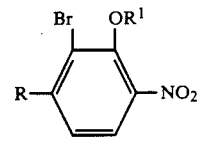

wherein R is $C_1$–$C_2$ alkyl, preferably methyl; formyl; cyano; carboxy or —$CO_2R^a$ wherein $R^a$ is $C_1$–$C_4$ alkyl, preferably ethyl, most preferably R is —$CO_2C_2H_5$ and $R^1$ is $C_1$–$C_4$ alkyl, preferably $C_1$–$C_2$ alkyl; $C_1$–$C_4$ haloalkyl; —$CH_2CH_2OCH_3$; —$CH_2CH_2OC_2H_5$, —$CH_2CH_2SCH_3$ or —$CH_2CH_2SC_2H_5$ with the proviso that when R is carboxy, then $R^1$ is —$CH_2CH_2OCH_3$, —$CH_2CH_2OC_2H_5$, —$CH_2CH_2SCH_3$ or —$CH_2CH_2SC_2H_5$, with the proviso that when R is carboxy, then $R^1$ is —$CH_2CH_2OCH_3$; —$CH_2CH_2OC_2H_5$; —$CH_2CH_2SCH_3$ or —$CH_2CH_2SC_2H_5$.

Embodiment E relates to novel intermediate compounds having the structural formula

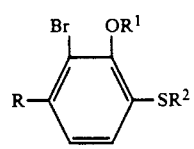

wherein R is $C_1$–$C_2$ alkyl, preferably methyl; formyl; cyano; carboxy or —$CO_2R^a$ wherein $R^a$ is $C_1$–$C_4$ alkyl, preferably ethyl, most preferably R is —$CO_2C_2H_5$; $R^1$ is $C_1$-$C_4$ alkyl; $C_1$-$C_4$ haloalkyl; —$CH_2CH_2OCH_3$, —$CH_2CH_2OC_2H_5$, —$CH_2CH_2SCH_3$ or —$CH_2CH_2SC_2H_5$ and $R^2$ is $C_1$-$C_4$ alkyl, preferably methyl, ethyl or n-propyl with the proviso that when R is carboxy, then $R^1$ is —$CH_2CH_2OCH_3$, —$CH_2CH_2OC_2H_5$, —$CH_2CH_2SCH_3$ or —$CH_2CH_2SC_2H_5$.

Embodiment F relates to novel intermediate compounds having the structural formula

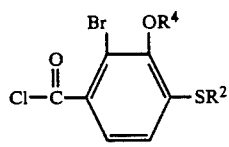

wherein $R^4$ is —$CH_2CH_2OCH_3$, —$CH_2CH_2OC_2H_5$, —$CH_2CH_2SCH_3$ or —$CH_2CH_2SC_2H_5$, preferably —$CH_2CH_2OCH_3$ or —$CH_2CH_2OC_2H_5$; and $R^2$ is $C_1$-$C_4$ alkyl, preferably methyl, ethyl or n-propyl.

Embodiment G relates to novel intermediate compounds having the structural formula

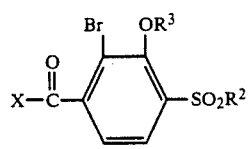

wherein X is hydroxy or chlorine; $R^3$ is —$CH_2CH_2OCH_3$ or —$CH_2CH_2CO_2H_5$ and $R^2$ is $C_1$-$C_4$ alkyl, preferably methyl, ethyl or n-propyl.

Embodiment H relates to novel intermediate compounds having the structural formula

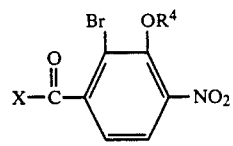

wherein X is hydroxy or chlorine and $R^4$ is —$CH_2CH_2OCH_3$, —$CH_2CH_2OC_2H_5$, —$CH_2CH_2SCH_3$, or —$CH_2CH_2SC_2H_5$, preferably —$CH_2CH_2OCH_3$ or —$CH_2CH_2OC_2H_5$.

Embodiment I relates to novel intermediate compounds having the structural formula

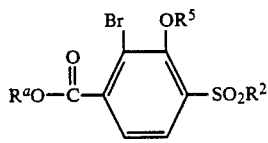

wherein $R^a$ is $C_1$-$C_4$ alkyl, preferably ethyl, $R^5$ is $C_1$-$C_4$ alkyl; $C_1$-$C_4$ haloalkyl; —$CH_2CH_2OCH_3$ or —$CH_2CH_2OC_2H_5$; preferably —$CH_2CH_2OCH_3$ or —$CH_2CH_2OC_2H_5$ and $R^2$ is $C_1$-$C_4$ alkyl, preferably methyl, ethyl or n-propyl.

In embodiments A-E, the group R can also be trifluoromethyl.

The trisubstituted benzoic acid chloride intermediates are useful in the preparation of the previously described herbicidal 2-(2',3',4'-trisubstituted benzoyl)-1,3-cyclohexanediones.

The several intermediate compounds of this invention can be prepared by the general method shown in the Figure of the next page with R, $R^1$, $R^2$ and $R^5$ being as defined. The groups $R^X$ and $R^Z$ and $C_1$-$C_4$ alkyl.

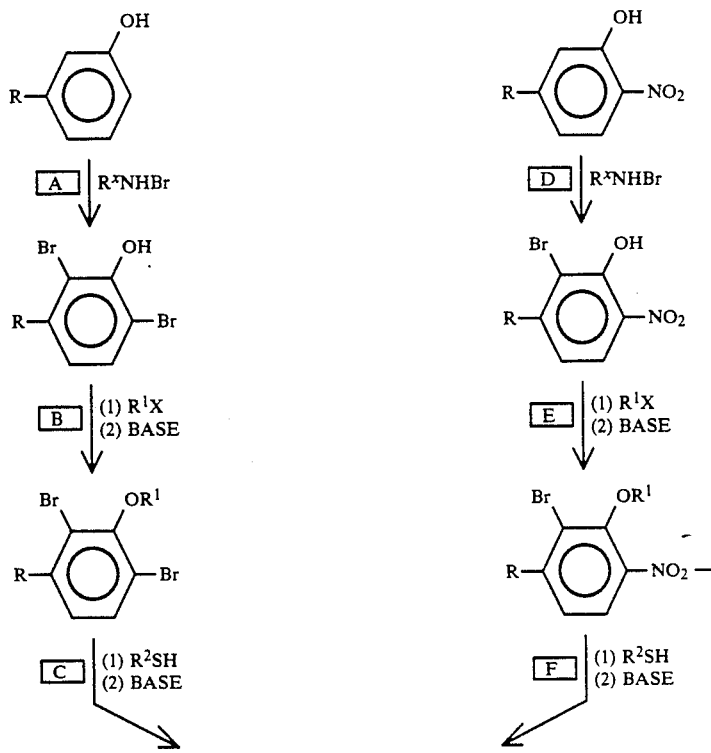

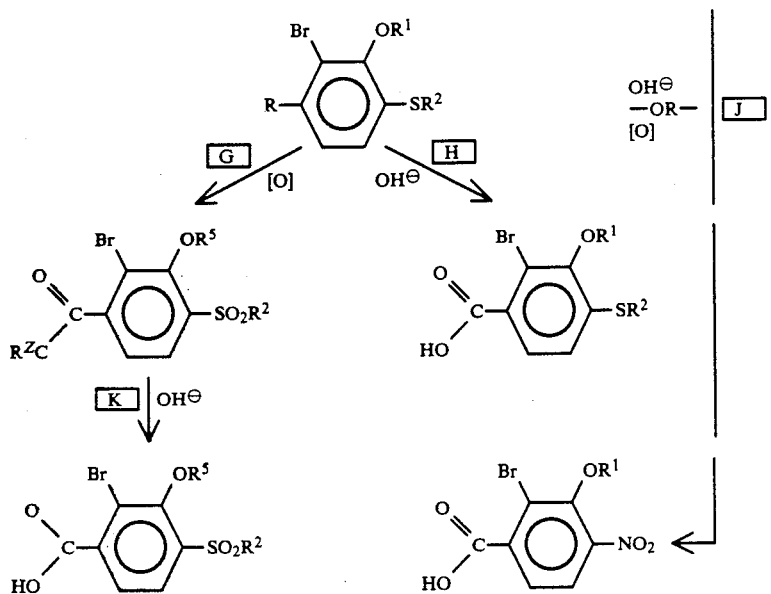

Referring to the Figure, and particularly to Reaction Steps (A) through (J), consider the following:

Generally in Reaction Step (A), a mole amount of the 3-substituted phenol is reacted with 2 moles of the brominating agent N-bromo $C_1-C_4$ alkylamine, preferably N-bromo tetra-butyl amine in a solvent such as methylene chloride at a temperature between $-70°$ C. to $25°$ C. After this reaction, the free brominated phenol is formed by reaction with a strong acid such as HCl. The N-bromo $C_1-C_4$ alkyl amine can be prepared by a reaction of 2 moles of $C_1-C_4$ alkyl amine and a mole of bromine in a solvent such as methylene chloride at low temperatures to yield one mole of N-bromo $C_1-C_4$ alkyl amine. The final reaction product is recovered by conventional techniques.

For Reaction Step (B), one mole of the dibromo-substituted phenol reaction product of Step (A) is reacted with an appropriate alkylating agent such as a 2-chloroethyl ethyl ether, 2-chloroethyl methyl ether, 2-chloroethyl methyl sulfide, 2-chloroethyl ethyl sulfide or $C_1-C_4$ alkylchloride along with a catalytic amount of potassium iodide and a mole excess of a base such as potassium carbonate. Alkyl iodides such as methyl iodide or ethyl iodide may also be used. In these cases the catalytic potassium iodide is not needed and little or no heat is required. The reaction is run at $50°$ C. to $80°$ C. for 4 hours with agitation. The reaction product is recovered by conventional techniques.

For Reaction Step (C), the dibromo compound from Reaction Step (B) is reacted with an equal mole amount of a $C_1-C_4$ alkyl mercaptan along with a mole excess of a base such as potassium carbonate in a solvent such as dimethylformamide. The reaction is run for several hours at a temperature between $50°$ C. to $100°$ C. with stirring under an inert atmosphere such as nitrogen. The desired reaction product is recovered by conventional techniques.

Generally, in Reaction Step (D), a mole amount of the 2-nitro-4-substituted phenol is monobrominated with a mole amount of the brominating agent N-bromo-$C_1-C_4$-alkyl amine according to the general procedure described for Reaction Step (A). 3-hydroxy-4-nitrobenzoic acid is the least preferred reactant because it results in a less pure preparation of 2-bromo-3-hydroxy-4-nitrobenzoic acid. Preferably an alkyl ester of 3-hydroxy-4-nitrobenzoic acid is used. The ester can be prepared by conventional synthesis using concentrated sulfuric acid in a solution of alkanol such as ethanol.

Reaction Step (E) is run using the general procedure of Step (B). Mole amounts of the phenol and the alkylating agent are used.

For Reaction Step (F) the procedure of Step (C) is used. The displacement of the nitro group by the mercaptan is essentially quantitative and occurs at temperatures from $0°$ C. to $25°$ C.

For Reaction Step (G) a mole amount of the alkyl ester of 2-bromo-4-alkylthio benzoic is oxidized with at least 3 moles of an oxidizing agent such as m-chloroperbenzoic acid in a suitable solvent such as methylene chloride by stirring a solution of the reactants at $20°$ to $100°$ C. The desired intermediate is recovered by conventional techniques. During this reaction step the alkylthio substituent is oxidized to the corresponding alkylsulfone.

For Reaction Step (H) a mole amount of the 2-bromo-3-substituted-4-alkylthio ester or cyano compound is hydrolyzed with a base such as sodium hydroxide to the corresponding 2-bromo-3-substituted-4-alkylthio benzoic acid. The hydrolysis is run in a solvent such as an 80 percent methanol-water mixture. The reaction can be run at $25°-100°$ C. with stirring. The desired product is recovered by conventional techniques.

For Reaction Step (J) when "R" is cyano or an ester group a mole amount of the appropriate 2-bromo-3-substituted-4-nitro compound is hydrolyzed with a base such as sodium hydroxide to the corresponding 2-bromo-3-substituted-4-nitro benzoic acid. The hydrolysis is run in a solvent such as an 80 percent methanol-water mixture. The reaction can be run at $25°-100°$ C. with stirring. The desired product is recovered by conventional techniques. When "R" is formyl, methyl or ethyl, a mole amount of the appropriate 2-bromo-3-substituted-4-nitro compound is oxidized to the corresponding trisubstituted benzoic acid with an excess of an oxidizing agent such as potassium permanganate or sodium hypochloride according to the known procedures.

For Reaction Step (K) the alkyl ester of the trisubstituted benzoic acid is converted to the trisubstituted benzoic acid by the hydrolysis step taught in Reaction Step (H).

The intermediate benzoic acids described herein can easily be converted to their respective acid chlorides and then to their acid cyanides, if desired, by the following two reactions. First, a mole of oxalyl chloride and a catalytic amount of dimethylformamide in a suitable solvent such as methylene chloride at a temperature of 20° to 40° C. for 1 to 4 hours is heated with a mole of the intermediate benzoic acid. The corresponding benzoic acid cyanide can easily be prepared from the benzoic acid chloride by reaction with cuprous cyanide at a temperature of 50° to 220° C. for 1 to 2 hours.

The following series of examples teach the synthesis of representative intermediate compounds of this invention. The structures of all compounds of the examples and tables were verified by nuclear magnetic resonance (NMR), infrared spectroscopy (IR) and mass spectroscopy (MS).

EXAMPLE 1

Ethyl 2,4-dibromo-3-hydroxybenzoate

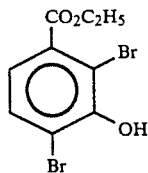

Using a procedure similar to that described (D. E. Pearson, R. D. Wysong and C. V. Breder in *J. Org. Chem.* 32, 2358 [1967]), to a 1-liter, 3-neck flask equipped with a mechanical stirrer, a nitrogen inlet and a pressure equalizing addition funnel was added 59 grams (g) of t-butyl amine (0.8 mole) in 400 milliliters (ml) of methylene chloride. This mixture was cooled to −65° C. with dry ice/isopropanol. To the cooled solution was slowly added (1 hour) 64 grams (0.4 mole [m]) of bromine diluted in 50 ml of methylene chloride. After the addition was complete, the mixture was stirred for 1 hour at approximately −60° C. Ethyl 3-hydroxyenzoate (0.2 mole 33.2 grams) was added, in one portion, to the cooled reaction mixture. This mixture was allowed to warm to room temperature overnight. The white solid was filtered off and washed with a minimum amount of methylene chloride and converted to the free phenol (ethyl 2,4-dibromo-3-hydroxybenzoate) using 500 ml methylene chloride and 400 ml of 2 Normal (N) hydrochloric acid. Gas chromatography indicated the product (49 g) was 92% pure. This material was a viscous oil.

Additional compounds were prepared by the same procedure as described in Example 1 and are listed in Table 1.

TABLE 1

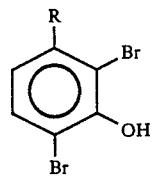

| R | Physical Constant (m.p. °C.) |
|---|---|
| CN | 194–198 |
| $CO_2CH_3$ | 74–75 |
| $CO_2H$ | 198–200 |
| CHO | 135–136 |
| $CF_3$ | 58–61 |

EXAMPLE 2

Ethyl 2,4-dibromo-3-(2-methoxyethoxy) benzoate

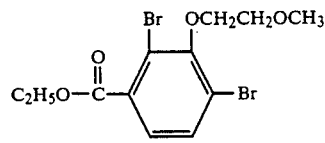

The ethyl ester from Example 1 (32.4 g, 0.1 mole) was dissolved in 200 ml of dimethyl formamide (DMF) and an excess of potassium carbonate (27.6 g, 0.2 mole) and 2-chloroethyl methyl ether (18.8 g, 0.2 mole) along with a catalytic amount of potassium iodide (4.8 g, 0.03 mole) were added. This reaction mixture was vigorously stirred and maintained at 70° C. for 4 hours. Normal workup gave 31.8 g of ethyl 2,4-dibromo-3-(2-methoxyethoxy) benzoate as an oil, 94% pure by gas chromatography. This ester would readily be hydrolyzed to its acid via the method described in Example 7.

Additional compounds were prepared by the same procedure as described in Example 2 (except in those cases using an alkyl iodide, the potassium iodide catalyst was omitted and little or no heat was required) and are listed in Table 2.

TABLE 2

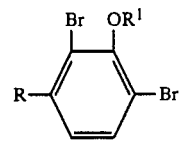

| R | $R^1$ | Physical Constant (m.p. °C.) |
|---|---|---|
| $CO_2C_2H_5$ | $CH_3$ | oil |
| $CO_2C_2H_5$ | $n-C_3H_7$ | oil |
| $CO_2H$ | $CH_3$ | 115–117 |
| $CO_2C_2H_5$ | $CH_2CH_2Br$ | oil |
| $CO_2H$ | $n-C_4H_9$ | 112–115 |
| $CO_2H$ | $C_2H_4OC_2H_5$ | 65–70 |
| $CO_2H$ | $C_2H_4SCH_3$ | oil |
| $CO_2C_2H_5$ | $CH_2CF_3$ | 41–43 |
| $CO_2H$ | $CH_2CF_3$ | 135–138 |
| $CO_2H$ | $C_2H_4OCH_3$ | 75–80 |
| $CO_2C_2H_5$ | $C_2H_4SCH_3$ | oil |
| $CO_2C_2H_5$ | $n-C_4H_9$ | oil |

EXAMPLE 3

Ethyl 2-bromo-3-(2-methoxyethoxy)-4-ethylthiobenzoate

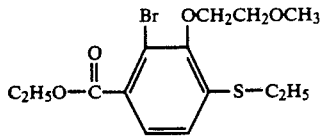

Ethyl 2,4-dibromo-3-(2-methoxyethoxy) benzoate (15.3 g, 0.04 mole) was dissolved in 125 ml of DMF and potassium carbonate (13.8 g, 0.1 mole) and ethyl mercaptan (4 g, 0.064 mole) were added. This mixture was heated at 70° C., under nitrogen, with vigorous stirring, for 4 hours. Normal workup gave 14.3 g of crude product (82% desired product by gas chromatography), ethyl 1-bromo-3-(2-methoxyethoxy)-4-ethylthiobenzoate as a viscous oil. This ester could readily be hydrolyzed to its free acid via the method described in Example 7. The crude ester was purified via silica chromatography using ether/pentane to give 11.2 g of pure product as an oil. The above-prepared ester was hydrolyzed to the corresponding acid according to the procedure described in Example 8.

Additional compounds were prepared by the same procedures as described in Example 3 and are listed in Table 3.

TABLE 3

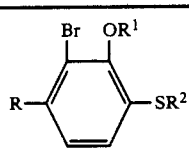

| R | $R^1$ | $R^2$ | Physical Constant (m.p. °C.) |
|---|---|---|---|
| $CO_2C_2H_5$ | $C_2H_5$ | $C_2H_5$ | 51–53 |
| $CO_2H$ | $C_2H_5$ | $C_2H_5$ | 112–115 |
| $CO_2C_2H_5$ | $C_2H_5$ | n-$C_3H_7$ | oil |
| $CO_2C_2H_5$ | $CH_3$ | n-$C_3H_7$ | oil |
| $CO_2H$ | $C_2H_5$ | n-$C_3H_7$ | 100–104 |
| $CO_2H$ | $CH_3$ | n-$C_3H_7$ | 135–138 |
| $CO_2C_2H_5$ | n-$C_3H_7$ | n-$C_3H_7$ | oil |
| $CO_2H$ | n-$C_3H_7$ | $CH_3$ | 150–152 |
| $CO_2H$ | n-$C_3H_7$ | $C_2H_5$ | 107–110 |
| $CO_2C_2H_5$ | n-$C_3H_7$ | $CH_3$ | oil |
| $CO_2C_2H_5$ | $CH_3$ | $CH_3$ | oil |
| $CO_2H$ | $CH_3$ | $CH_3$ | 165–167 |
| $CO_2C_2H_5$ | $C_2H_4SCH_3$ | $C_2H_5$ | oil |
| $CO_2C_2H_5$ | $C_2H_4OCH_3$ | $CH_3$ | oil |
| $CO_2C_2H_5$ | $C_2H_4OC_2H_5$ | $CH_3$ | oil |
| $CO_2C_2H_5$ | $C_2H_4OCH_3$ | n-$C_3H_7$ | oil |

EXAMPLE 4

Ethyl 2-bromo-3-hydroxy-4-nitrobenzoate

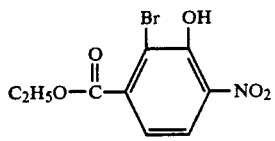

A 0.1 mole of the ethyl ester of 3-hydroxy-4-nitrobenzoic acid was monobrominated using the procedure described in Example 1, except only one equivalent of bromine and two equivalents of t-butyl amine were used. This reaction yielded ethyl 2-bromo-3-hydroxy-4-nitrobenzoate in 70.1% yield. It had a melting point of 58°–61° C.

The ethyl ester of 3-hydroxy-4-nitrobenzoic acid was prepared as follows:

To 100 g of 3-hydroxy-4-nitrobenzoic acid in 300 ml of ethanol was added 15 ml of concentrated sulfuric acid. This solution was refluxed for 3 hours and then a Dean-Stark trap was attached and 100 ml of ethanol-water was distilled off. The reaction mixture was cooled and poured onto 500 grams of ice. The resulting solid was collected, dissolved in 500 ml of ether and the ether solution was washed three times with 1% aqueous sodium bicarbonate. The ether layer was dried and concentrated to give 103.8 g of pure ester.

EXAMPLE 5

Ethyl 2-bromo-3-(2-methoxyethoxy)-4-nitrobenzoate

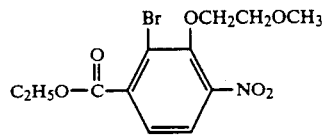

Using a procedure similar to that of Example 2, 0.2 moles of ethyl 2-bromo-3-hydroxy-4-nitrobenzoate and an excess of potassium carbonate (0.35 moles) and 2-chloroethyl methyl ether (0.35 moles) along with a catalytic amount of potassium iodide (7.2 g, 0.045 m) were combined with 350 ml of dimethylformamide. After heating at 70° C. for 4 hours, normal workup gave 0.187 moles of ethyl 2-bromo-3-(2-methoxyethoxy)-4-nitrobenzoate as a viscous oil. This ester can be readily hydrolyzed to its acid using the procedure of Example 8.

Additional compounds were prepared by the same procedure as described in Example 5 and are listed in Table 4.

TABLE 4

| R | Physical Constant (m.p. °C.) |
|---|---|
| $CO_2H$ | 63–68 |

Ethyl 2-bromo-3-(2-methoxyethoxy)-4-ethylthiobenzoate

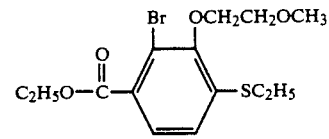

Using a procedure similar to that of Example 3, 0.1 mole of ethyl 2-bromo-3-(2-methoxyethoxy)-4-nitrobenzoate and an excess of potassium carbonate (0.2 mole) and a slight excess of ethyl mercaptan (0.125 mole) were combined in 200 ml of dimethylformamide at 0° C., under nitrogen. The reaction was stirred overnight at room temperature. Normal workup gave the desired product in essentially quantitative yield. This compound was compared to the product from Example 3 and they were identical by all spectroscopic and chromatographic comparisons.

EXAMPLE 7

Ethyl 2-bromo-3-(2-methoxyethoxy)-4-ethylsulfonyl benzoate

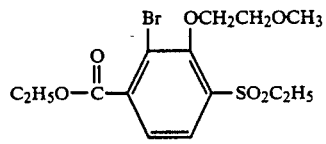

The ester, ethyl 2-bromo-3-(2-methoxyethoxy)-4-ethylthiobenzoate from Example 3 (12 g) was dissolved in 100 ml of methylene chloride and solid m-chloroperoxybenzoic acid (85% pure, 0.1 mole) was added slowly over a period of 2 hours. The crude reaction mixture was stirred overnight. The excess peracid was destroyed with sodium bisulfite (100 ml, 5%, solution). The organic layer was washed three times with base, dried, concentrated and chromatographed on silica gel ($CH_2Cl_2/(C_2H_5)_2O$) to give 8.3 grams of pure ethyl 2-bromo-3-(2-methoxyethoxy)-4-ethylsulfonylbenzoate as a viscous oil.

Additional compounds were prepared by the same procedure as described in Example 7 and are listed in Table 5.

TABLE 5

$$R^bOC\text{-}\underset{\underset{SO_2R^2}{\text{Br OR}^1}}{\bigcirc}$$

| $R^b$ | $R^1$ | $R^2$ | Physical Constant (m.p. °C.) |
|---|---|---|---|
| $C_2H_5$ | $C_2H_5$ | $C_2H_5$ | oil |
| $C_2H_5$ | n-$C_3H_7$ | $CH_3$ | 84–87 |
| $C_2H_5$ | $C_2H_4OCH_3$ | n-$C_3H_7$ | oil |
| $C_2H_5$ | $C_2H_4OCH_3$ | $CH_3$ | oil |
| $C_2H_5$ | n-$C_5H_{11}$ | $C_2H_5$ | 58–59 |
| $C_2H_5$ | n-$C_4H_9$ | $C_2H_5$ | 45–49 |

EXAMPLE 8

2-bromo-3-(2-methoxyethoxy)-4-ethylsulfonybenzoic acid

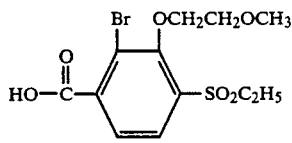

To 7.26 g (0.02 mole) of the ethyl 2-bromo-3-(2-methoxyethoxy)-4-ethylsulfonylbenzoate in 50 ml of 80% methanol/water was added 1.2 g (0.03 mole) of sodium hydroxide. After stirring at room temperature overnight, 100 ml of ether was added and the organic phase was extracted three times with 50 ml of 1N NaOH. The combined base extracts were acidified and extracted three times with methylene chloride. The methylene chloride was dried and concentrated to yield 6.6 grams of 2-bromo-3-(2-methoxy-ethoxy)-4-ethylsulfonylbenzoic acid as a viscous oil.

Additional compounds were prepared by the same procedure as described in Example 5 and are listed in Table 6.

TABLE 6

$$HO\text{-}C\text{-}\underset{\underset{SO_2R^2}{\text{Br OR}^1}}{\bigcirc}$$

| $R^1$ | $R^2$ | Physical Constant (m.p. °C.) |
|---|---|---|
| $C_2H_5$ | $C_2H_5$ | oil |
| n-$C_3H_7$ | $CH_3$ | 155–160 |
| $CH_3$ | n-$C_3H_7$ | 145–149 |
| $CH_3$ | $CH_3$ | 130–135 |
| $C_2H_4OCH_3$ | n-$C_3H_7$ | 112–115 |
| $C_2H_4OCH_3$ | $CH_3$ | oil |

The above-described benzoic acids can be readily converted to their acid chlorides using oxalyl chloride and a catalytic amount of dimethylformamide. These acid chlorides can be reacted with the above-described 1,3-cyclohexanedione to prepare the above-described herbicidal 2,3,4-trisubstituted benzoyl-1,3-cyclohexanediones according to the following two-step reaction:

The process proceeds via the production of an enol ester intermediate as shown in reaction (1). The final product is obtained by rearrangement of the enol ester as shown in reaction (2). The two reactions may be conducted as separate steps by isolation and recovery of the enol ester using conventional techniques prior to conducting step (2), or by addition of a cyanide source to the reaction medium after the formation of the enol ester, or in one step by inclusion of the cyanide source at the start of reaction (1).

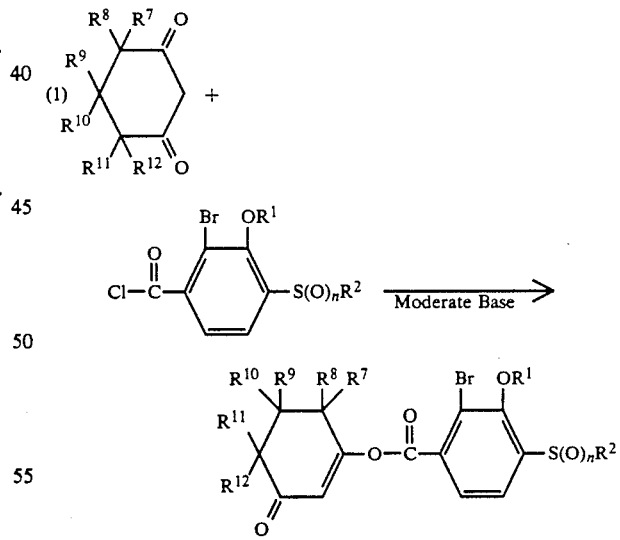

wherein n and $R^1$, $R^2$ and $R^7$ through $R^{12}$ are as defined above and the moderate base is such as tri-$C_1$-$C_6$ alkylamine, pyridine, alkali metal carbonate or alkali metal phosphate.

Generally, in step (1) mole amounts of the dione and substituted benzoyl chloride are used, along with a slight mole excess of a moderate base. The two reactants are combined in an organic solvent such as acetonitrile, methylene chloride, toluene, ethyl acetate or dimethylformamide. The base and benzoyl reactant preferably are added to the reaction mixture with cooling. The mixture is stirred at 0° C.-50° C. until the reaction is substantially complete.

The reaction product is worked up by conventional techniques.

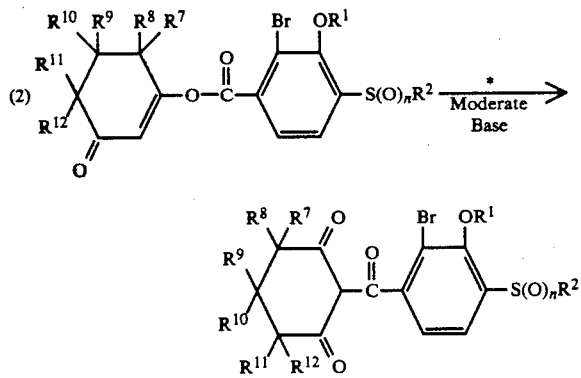

wherein $R^1$, $R^2$ and $R^7$ through $R^{12}$ are as defined above.

Generally, in step (2) a mole of the enol ester intermediate is reacted with 1 to 4 moles of the base, preferably about 2 moles of moderate base and from 0.01 mole to about 0.5 mole or higher, preferably around 0.1 mole of the cyanide source (e.g., potassium cyanide or acetone cyanohydrin). The mixture is stirred in a reaction pot until the rearrangement is substantially complete at a temperature below 80° C., preferably about 20° C. to about 40° C., and the desired product is recovered by conventional techniques.

The term "cyanide source" refers to a substance or substances which under the rearrangement conditions consists of or generates hydrogen cyanide and/or cyanide anion.

The process is conducted in the presence of a catalytic amount of a source of cyanide anion and/or hydrogen cyanide, together with a molar excess, with respect to the enol ester, of a moderate base.

Preferred cyanide sources are alkali metal cyanides such as sodium and potassium cyanide; cyanohydrins of methyl alkyl ketones having from 1-4 carbon atoms in the alkyl groups, such as acetone or methyl isobutyl ketone cyanohydrins; cyanohydrins of benzaldehyde or of $C_2$-$C_5$ aliphatic aldehydes such as acetaldehyde, propionaldehyde, etc., cyanohydrins; zinc cyanide; and hydrogen cyanide itself. Hydrogen cyanide is considered most advantageous as it produces relatively rapid reaction and is inexpensive. Among cyanohydrins the preferred cyanide source is acetone cyanohydrin.

The cyanide source is used in an amount up to about 50 mole % based on the enol ester. It may be used in as little as about 1 mole % to produce an aceptable rate of reaction at about 40° C. on a small scale. Larger scale reactions give more reproducible results with slightly higher catalyst levels of about 2 mole %. Generally about 1–10 mole % of the cyanide source is preferred.

The process is conducted with a molar excess, with respect to the enol ester, of a moderate base. By the term "moderate base" is meant a substance which acts as a base yet whose strength or activity as a base lies between that of strong bases such as hydroxides (which could cause hydrolysis of the enol ester) and that of weak bases such as bicarbonates (which would not function effectively). Moderate bases suitable for use in this embodiment include both organic bases such as tertiary amines and inorganic bases such as alkali metal carbonates and phosphates. Suitable tertiary amines include trialkylamines such as triethylamine, trialkanolamines such as triethanolamine, and pyridine. Suitable inorganic bases include potassium carbonate and trisodium phosphate.

The base is used in an amount of from about 1 to about 4 moles per mole of enol ester, preferably about 2 moles per mole.

When the cyanide source is an alkali metal cyanide, particularly potassium cyanide, a phase transfer catalyst may be included in the reaction. Particularly suitable phase transfer catalysts are the Crown ethers.

A number of different solvents may be usable in this process, depending on the nature of the acid chloride or the acylated product. A preferred solvent for this reaction is 1,2-dichloroethane. Other solvents which may be employed depending on the reactants or products include toluene, acetonitrile, methylene chloride, ethyl acetate, dimethylformamide, and methyl isobutyl ketone (MIBK).

In general, depending on the nature of the reactants and the cyanide source, the rearrangement may be conducted at temperatures up to about 50° C.

What is claimed is:

1. A compound having the structural formula

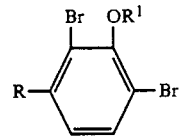

wherein R is $C_1$-$C_2$ alkyl, formyl, cyano, carboxy or $CO_2R^a$ wherein $R^a$ is $C_1$-$C_4$ alkyl and $R_1$ is $C_1$-$C_4$ haloalkyl, —$CH_2CH_2OCH_3$, —$CH_2CH_2OC_2H_5$, —$CH_2CH_2SCH_3$ or —$CH_2CH_2SC_2H_5$, with the proviso that when R is carboxy, then $R_1$ is —$CH_2CH_2OCH_3$; —$CH_2CH_2OC_2H_5$; —$CH_2CH_2SCH_3$ or $CH_2CH_2SC_2H_5$.

2. The compound of claim 1 wherein R is carboethoxy or carboxy and $R^1$ is $C_1$-$C_4$ alkyl, —$CH_2CH_2OCH_3$, —$CH_2CH_2OC_2H_5$, or —$CH_2CH_2SCH_3$.

3. The compound of claim 1 wherein R is carboethoxy and $R^1$ is —$CH_2CH_2OCH_3$.

4. A compound of the structural formula

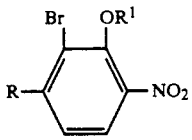

wherein R is $C_1$-$C_2$ alkyl, formyl, cyano, carboxy or —$CO_2R^a$ wherein $R^a$ is $C_1$-$C_4$ alkyl, $R^1$ is $C_1$-$C_4$ haloalkyl; —$CH_2CH_2OCH_3$; —$CH_2CH_2OC_2H_5$; —$CH_2CH_2SCH_3$; —$CH_2CH_2SC_2H_5$ with the proviso that when R is carboxy, then $R^1$ is only —$CH_2CH_2OCH_3$, —$CH_2CH_2OC_2H_5$, —$CH_2CH_2SCH_3$ or —$CH_2CH_2SC_2H_5$.

5. The compound of claim 4 wherein R is carboethoxy and $R^1$ is —$CH_2CH_2OCH_3$.

6. A compound having the structural formula

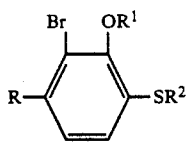

wherein R is methyl, ethyl, formyl, cyano, carboxy or —$CO_2R^a$ wherein $R^a$ is $C_1$-$C_4$ alkyl; $R^1$ is $C_1$-$C_4$ alkyl, $C_1$-$C_4$ haloalkyl, —$CH_2CH_2OCH_3$, —$CH_2CH_2OC_2H_5$, —$CH_2CH_2SCH_3$ or —$CH_2CH_2SC_2H_5$ and $R^2$ is $C_1$-$C_4$ alkyl with the proviso that when R is carboxy, then $R^1$ is only —$CH_2CH_2OCH_3$, —$CH_2CH_2OC_2H_5$, —$CH_2CH_2SCH_3$ or —$CH_2CH_2SC_2H_5$.

7. The compound of claim 6 wherein R is carboethoxy or carboxy, $R^1$ is $C_1$-$C_4$ alkyl, —$CH_2CH_2OCH_3$, —$CH_2CH_2OC_2H_5$ or —$CH_2CH_2$—$SCH_3$; and $R^2$ is $C_1$-$C_4$ alkyl.

8. The compound of the structural formula

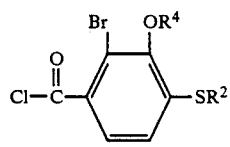

wherein $R^4$ is —$CH_2CH_2OCH_3$, —$CH_2CH_2OC_2H_5$, —$CH_2CH_2SCH_3$ or —$CH_2CH_2SC_2H_5$ and $R^2$ is $C_1$-$C_4$ alkyl.

9. The compound of claim 8 wherein $R^4$ is —$CH_2CH_2OCH_3$ and $R^2$ is $C_1$-$C_4$ alkyl.

10. A compound having the structural formula

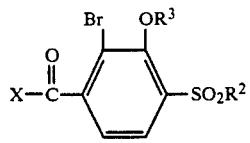

wherein $R^3$ is —$CH_2CH_2OCH_3$, —$CH_2CH_2OC_2H_5$, X is hydroxy or chlorine; and $R^2$ is $C_1$-$C_4$ alkyl.

11. The compound of claim 10 wherein X is hydroxy or chlorine; $R^3$ is —$CH_2CH_2OCH_3$, and $R^2$ is $C_1$-$C_4$ alkyl.

12. The compound of claim 10 wherein X is chlorine.

13. The compound of claim 10 wherein X is hydroxy.

14. A compound of the structural formula

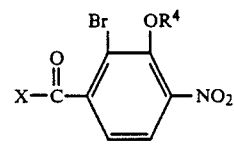

wherein X is hydroxy or chlorine; $R^4$ is —$CH_2CH_2OCH_3$, —$CH_2CH_2OC_2H_5$, —$CH_2CH_2SCH_3$ or —$CH_2CH_2SC_2H_5$.

15. The compound of claim 14 wherein X is chlorine and $R^4$ is —$CH_2CH_2OCH_3$ or —$CH_2CH_2OC_2H_5$.

16. The compound of claim 14 wherein X is hydroxy and $R^4$ is —$CH_2CH_2OCH_3$ or —$CH_2CH_2OC_2H_5$.

17. A compound of the structural formula

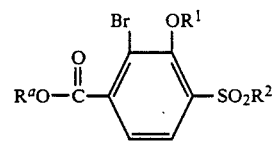

wherein $R^a$ is $C_1$-$C_4$ alkyl, $R^1$ is $C_1$-$C_4$ alkyl; $C_1$-$C_4$ haloakyl; —$CH_2CH_2OCH_3$; —$CH_2CH_2OC_2H_5$; and $R^2$ is $C_1$-$C_4$ alkyl.

18. The compound of claim 17 wherein $R^a$ is ethyl; $R^1$ is —$CH_2CH_2OCH_3$; or —$CH_2CH_2OC_2H_5$ and $R^2$ is $C_1$-$C_3$ alkyl.

* * * * *

UNITED STATES PATENT AND TRADEMARK OFFICE
CERTIFICATE OF CORRECTION

PATENT NO. : 5,026,896
DATED : June 25, 1991
INVENTOR(S) : William J. Michaely

It is certified that error appears in the above-indentified patent and that said Letters Patent is hereby corrected as shown below:

In Column 14, line 38, after "$R_1$ is" insert $--C_1-C_4$ alkyl,--.

In Column 14, line 59, after "$R^1$ is" insert $--C_1-C_4$ alkyl;--.

Signed and Sealed this

Fifth Day of April, 1994

Attest:

BRUCE LEHMAN

*Attesting Officer*     *Commissioner of Patents and Trademarks*